United States Patent
Loree, IV et al.

(10) Patent No.: US 8,096,960 B2
(45) Date of Patent: *Jan. 17, 2012

(54) EASY WAKE DEVICE

(76) Inventors: Leonor F Loree, IV, Atlanta, GA (US); Eric A. Toops, Hoschton, GA (US)

( * ) Notice: Subject to any disclaimer, the term of this patent is extended or adjusted under 35 U.S.C. 154(b) by 180 days.

This patent is subject to a terminal disclaimer.

(21) Appl. No.: 11/926,909

(22) Filed: Oct. 29, 2007

(65) Prior Publication Data

US 2008/0191885 A1      Aug. 14, 2008

Related U.S. Application Data

(63) Continuation-in-part of application No. 11/032,404, filed on Jan. 10, 2005, now Pat. No. 7,306,567.

(60) Provisional application No. 60/535,247, filed on Jan. 9, 2004.

(51) Int. Cl.
    *A61B 5/103* (2006.01)
    *A61B 5/117* (2006.01)

(52) U.S. Cl. ........................................ 600/595; 600/587

(58) Field of Classification Search .................. 600/595, 600/587

See application file for complete search history.

(56) References Cited

U.S. PATENT DOCUMENTS

| | | | |
|---|---|---|---|
| 4,228,806 A | | 10/1980 | Lidow |
| 5,928,133 A | * | 7/1999 | Halyak ............................ 600/26 |
| 6,361,508 B1 | | 3/2002 | Johnson et al. |
| 6,468,234 B1 | | 10/2002 | Van der Loos et al. |
| 6,547,728 B1 | | 4/2003 | Cornuejols |
| 2004/0049132 A1 | * | 3/2004 | Barron et al. .................. 600/595 |
| 2005/0012622 A1 | * | 1/2005 | Sutton ......................... 340/573.1 |
| 2006/0150734 A1 | | 7/2006 | Mimnagh-Kelleher et al. |

FOREIGN PATENT DOCUMENTS

| | | |
|---|---|---|
| DE | 19642316 | 4/1998 |
| JP | 8160172 | * 6/1996 |
| WO | WO9302731 | 2/1993 |

* cited by examiner

*Primary Examiner* — Max Hindenburg
*Assistant Examiner* — H. Q. Nguyen
(74) *Attorney, Agent, or Firm* — Smith Risley Tempel Santos LLC; Gregory Scott Smith; Matthew T. Hoots

(57) ABSTRACT

A device that monitors a user's sleep cycles and operates to sound an alarm to awaken the user at an optimal point within a sleep cycle. Once an alarm time is set and the alarm is activated, the device begins to monitor a wearer's sleep cycles by identifying the points in time at which the wearer moves his or her body limbs. As the alarm time is approached, the device can trigger the alarm earlier if the wearer is at an optimal point in the sleep cycle or, even retard the triggering of the alarm if the optimal point in the sleep cycle is expected to occur shortly. The device can be used to assist children in waking up to prevent bed wetting, or in a patient for obtaining light therapy.

17 Claims, 10 Drawing Sheets

EASY WAKE DEVICE

CROSS-REFERENCE TO RELATED APPLICATIONS

This application is a continuation-in-part of United States Application for patent filed on Jan. 10, 2005 and assigned Ser. No. 11/032,404 now U.S. Pat. No. 7,306,567, which application claims the benefit of the filing date of United States Provisional Application for Patent filed on Jan. 9, 2004, having a title of EASY WAKE WRIST WATCH and having been assigned Ser. No. 60/535,247.

BACKGROUND OF THE INVENTION

The present invention is directed towards an apparatus and method for determining the optimal moments to awaken a user during the sleep cycle and, more specifically, it relates to an apparatus and method that detects motion of a sleeping user to determine the user's sleep cycle and may alter the triggering of an alarm condition based on the detection of the motion.

The human body is an amazingly complex electrical, chemical and physiological machine. In a world where technologists are all seeking "wireless" solutions, the human body has been operating in that mode since its earliest inception. Utilizing fuel ranging from BIG MACS with fries to pot roasts to SNICKERS bars, the human body is able to generate its own source of energy. Another extremely important requirement of the human body is down time. Although the amount of down time necessary for the human body can vary from person to person, everyone needs and requires some amount of down time, otherwise known as sleep.

Many studies have been performed around the concept of "sleep". From these studies it is well known that a period of sleep consists of several sleep cycles. Each sleep cycle spans a period of time that starts with a light or shallow state of unconsciousness, progresses to a deep state of unconsciousness, and then returns to the shallow state. It is also well known through empirical evidence that the human body is much more adept to recovering from a period of sleep when the individual is aroused out of the unconscious sleep state while in the shallow state. Being aroused from a deep state not only requires a longer recovery time, but can also adversely affect the individual's alertness and energy state throughout the day. Thus, there is a need in the art for a technique to arouse an individual from his or her sleep when the individual is within a shallow state of sleep.

Furthermore, there are certain reasons that may arise that require waking of a user during the middle of the night. For instance, it is often necessary for a patient to take medicine dosages during the night. Other situations also arise in which a subject needs to be aroused during the night. Having the ability to awaken such individuals at a point in time in which they will be most easily aroused would be beneficial. Thus, there is a need in the art for a mechanism to awaken people at certain times based on sleep cycle data for the individual.

It is also well known that when an individual is residing in a shallow state of sleep, there is a higher tendency for the individual to move parts of their body, such as their arms or legs. Thus, there is a need in the art for a technique to determine when an individual is in a shallow state of sleep and attempt to arouse the individual during this period of time.

SUMMARY OF THE INVENTION

The present invention combines a wrist watch and an accelerometer, or other motion detection device, into a single closed loop device for personal operation. The present invention operates to distinguish between the deep and shallow sleep cycles of an individual based on the individual's movements. During a shallow sleep cycle, individuals will have a tendency to move their limbs. The accelerometer detects such movements and identifies the user as being in a shallow sleep cycle. The user can set the wrist watch for a particular alarm time. If a shallow sleep cycle is detected during a particular window surrounding the set alarm time, the alarm may either be sounded early, or retarded to allow the user to be awakened at an optimal time.

DETAILED DESCRIPTION OF THE VARIOUS ASPECTS OF THE INVENTION

The present invention is directed towards a wrist watch type apparatus that includes an alarm mechanism. The alarm can be set to go off (a) at a particular time ("the programmed alarm"), (b) after a particular number of sleep cycles, or (c) a combination of the two.

When the device is set to go off at a particular time, the actual triggering of the alarm will depend upon motion detected by a motion detection apparatus. The operation of the invention is based on a correlation between body movement and a shallow portion of a person's sleep cycle. Thus, in a window of time around the programmed alarm, the present invention monitors the activity of the motion detector. If motion is detected within a certain period of time prior to the programmed alarm time, the alarm will trigger at an earlier time. If motion is not detected by the programmed alarm time, the triggering of the alarm will be delayed until either motion is detected or a threshold delay is reached.

Figure 4:
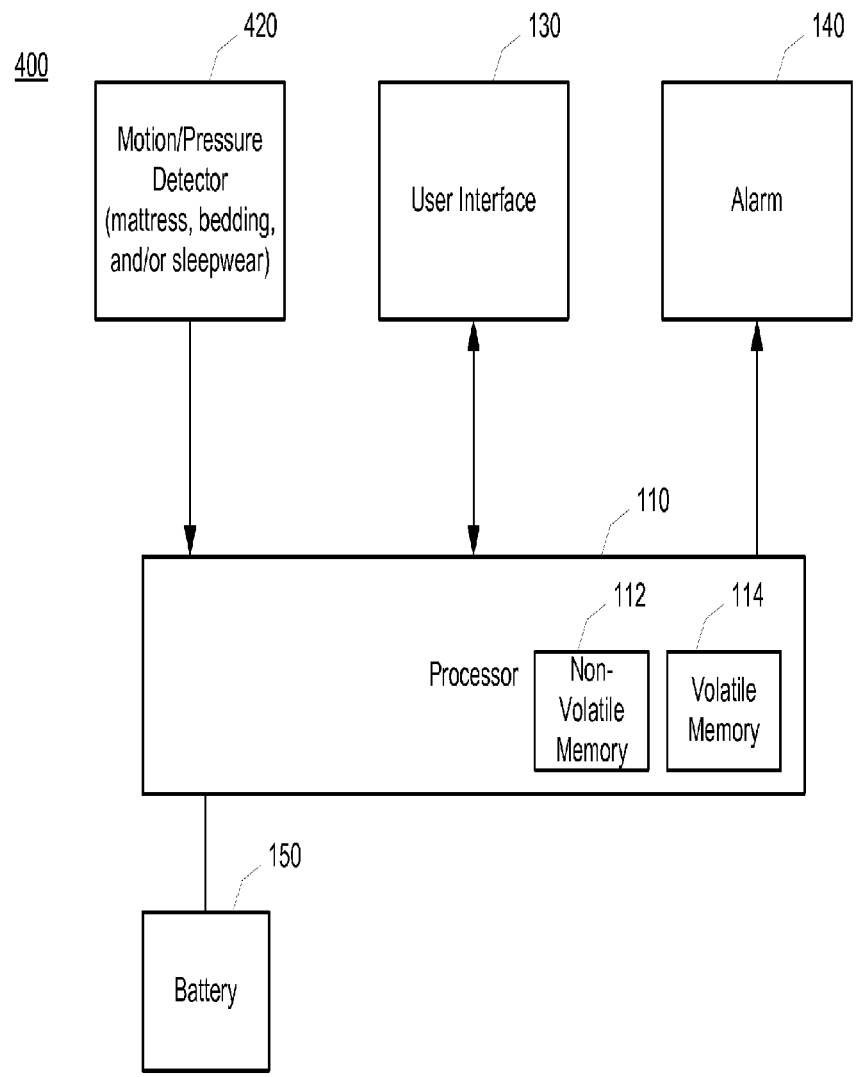
FIG. 4 is a block diagram illustrating the functional components of another exemplary embodiment of the invention.

In the preferred embodiment of the invention, the motion detection mechanism is an accelerometer. However, other methods of motion detection can also be used such as motion sensors embedded within a mattress or covering (see element 420 of embodiment 400 in FIG. 4), optical movement detection devices, or the like. In addition, in the preferred embodiment, the device is in the form of a wrist watch; however, other embodiments may also be utilized such as, but not limited to, a finger device, ankle device, leg device, a head band, and arm device.

Example of operation. As an example, the user sets the watch for a 7:00am wake up time and a 6:40am window. The window could be any of a variety of setting such as +/−10 minutes, +/−20 minutes, +10 minutes −20 minutes, −15 minutes, or the like. In the present example, if between the times of 6:40-7:00am the watch senses a particular type of movement, the alarm will be triggered early and the user will be awakened with almost no effort. The user will awake refreshed and feeling like they were hardly asleep. If in that 20-minute window the movement criteria are not met, the alarm will default to the 7:00am alarm and wake the user like a normal alarm clock.

In one embodiment of the invention, motion is only detected in a particular plane. However, it should be understood that all planes of movement could be detected in three dimensional planes.

The present invention may also employ the use of hysterisis. For instance, a particular amount of movement may be required to trigger an early alarm. If some movement is detected, the device may enter a "look for more movement" mode of operation. If a particular amount of movement is detected in this mode, then the alarm may be triggered. However, if no additional movement is detected for a particular period of time, the device may exit the "look for more movement" mode of operation and revert back to the normal mode in which any movement is monitored.

The present invention may also be used to track sleep cycles during the night and obtain and average time for a user's sleep cycles. Using this information, the present invention may be able to detect anomalies in the person's sleep cycle. In addition, the device can utilize the sleep cycle information to conduct predictive analysis of when the users next shallow sleep cycle will occur.

The device may also include a snooze capability, similar to standard alarm devices that allow a user to delay the alarm for a fixed period of time. In addition, the device can include a snooze capability that request the alarm to be delayed for an incremental number of sleep cycles. Using this aspect of the present invention, a user can set the device to alarm after a particular number of sleep cycles. Thus, the user can take a short nap of just one sleep cycle, or a longer number of sleep cycles.

The present invention can also operate to distinguish between movement occurring while the user is attempting to go to sleep and movement occurring as a part of a sleep cycle. For instance, if the user selects a particular number of sleep cycles before the alarm will sound, the device can require a threshold amount of time to occur in which no movement is detected prior to beginning the sleep cycle count. Advantageously, this aspect of the present invention allows a user to set the device for his or her optimal number of sleep cycles and, the device will wait until the sleep cycle process begins before counting, and then sound an alarm during the shallow sleep cycle of the desired sleep cycle.

As another example, a user may not have any particular time in mind that he or she wants to be awakened but knows that he or she functions better if he or she has slept for 6 sleep cycles. Thus, the user sets the device for 6 sleep cycles and retires for the night. Once the device determines that the user has entered into sleep cycles, it begins to count the sleep cycles. After 6 sleep cycles, the device will detect motion during the shallow portion of the cycle and then sound an alarm. As previously describe, the device can keep a running average of the user's sleep cycles. Thus, if for some reason a user goes through a shallow sleep cycle without any movement, the device can apply heuristics to determine such a condition. For example, if a person's sleep cycle typically lasts for 45 minutes and the device does not detect motion for 90 minutes, the device can determine that one shallow sleep state had been missed and adjust the sleep cycle count accordingly. In addition, if the device does not detect movement at the end of the selected number of sleep cycles, the device can conclude that the end of the sleep cycle has been reached and after a threshold period of time, trigger the alarm. For example, if the user programs the device for 6 sleep cycles and the device has determined the user's typical sleep cycle is 45 minutes, then after a particular number of minutes (i.e., 20 minutes) after the 6th sleep cycle was to be completed, the device may trigger the alarm.

The device may utilize a variety of alarm mechanisms and the present invention is not limited to any particular mechanism. Some exemplary mechanisms include an audible alarm, a vibrator or a blinking light. In addition, a wireless transmitter can be included in the device. The wireless transmitter can be used to trigger other alarm mechanisms that are equipped with a wireless receiver. For instance, user may wish to be awakened by a radio or a television. If the radio or television is equipped with an appropriate wireless receiver, when the device triggers the alarm, a turn on signal will be sent to the wireless receiver. A typical wireless transmitter and receiver solution could include BlueTooth technology or I.E.E.E. 802.11.

Figure 6:
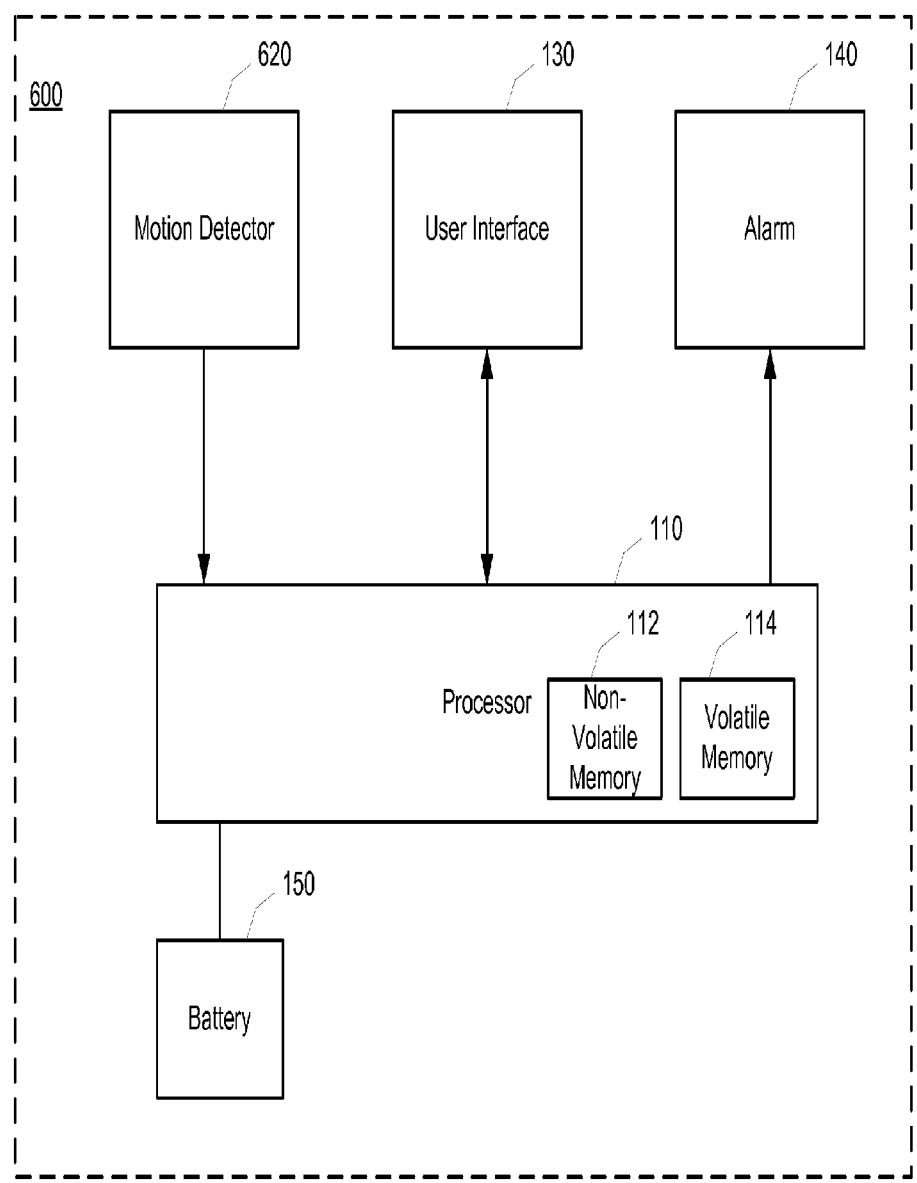
FIG. 6 is a block diagram illustrating the functional components of another exemplary embodiment of the invention.

Another aspect of the present invention is that it is self-contained in a single unit that can be worn on the body (see element 620 of embodiment 600 in FIG. 6). It is not necessary to have wires extending from the body to another device that performs any of the functions such as monitoring or calculating sleep cycles.

In other embodiments, the technology of the present invention can be incorporated into other objects that can also detect movement of the user. For instance, in one embodiment, the invention can be incorporated into a sleeping mattress or a pad that is placed over the top of a mattress. In this embodiment, accelerometers or pressure detection devices could be used (see element 420 of embodiment 400 in FIG. 4). In another embodiment, the invention can be incorporated in a blanket or comforter under which the user sleeps (see element 420 of embodiment 400 in FIG. 4). Yet in another embodiment, the invention can be incorporated into the user's sleepwear, such as pajamas or a night gown (see element 420 of embodiment 400 in FIG. 4).

Figure 1:
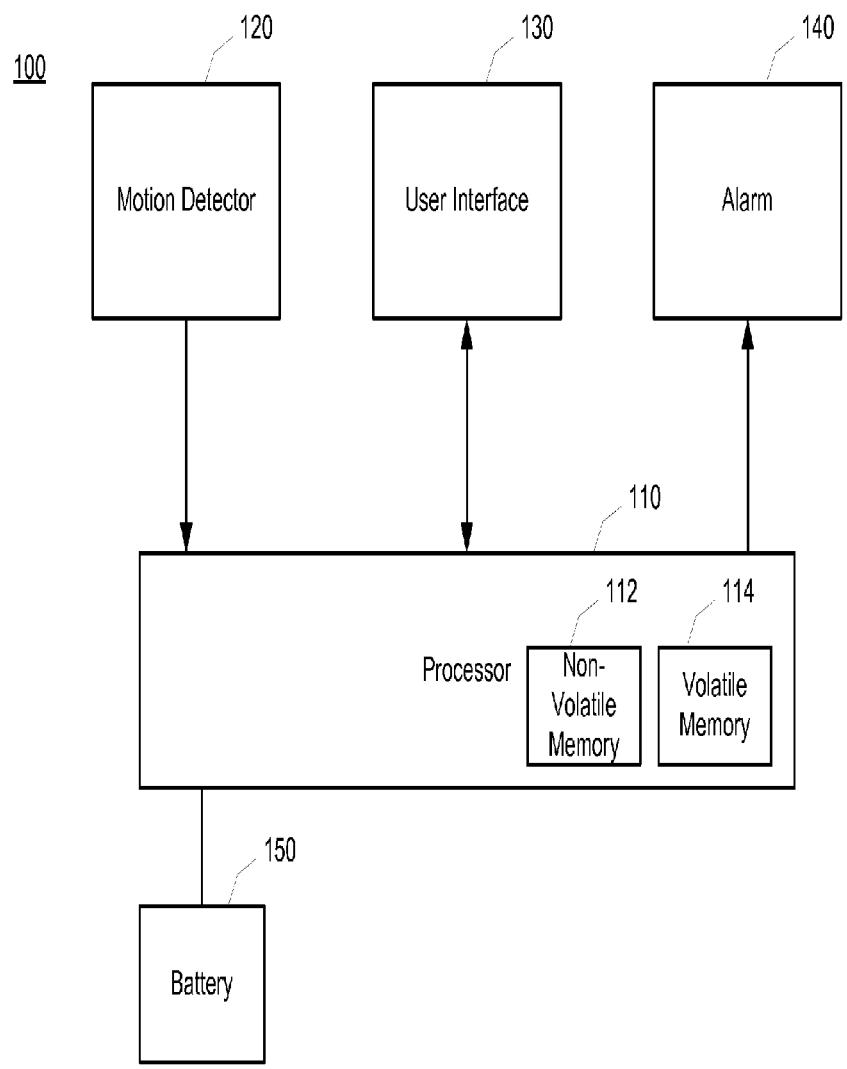
FIG. 1 is a block diagram illustrating the functional components of an exemplary embodiment of the present invention.

FIG. 1 is a block diagram illustrating the functional components of an exemplary embodiment of the present invention. The device 100 could be embodied within a wrist watch or some similar apparatus that can be worn on the body. The device 100 includes a processor 110 that is powered through a battery 150. The processor 110 interfaces to a motion detector 120, a user interface 130 and an alarm 140. As previously described, the motion detector can be an accelerometer or other motion sensing device embedded into the device 100, or may be an external device that is wireless coupled to the processor 110. The user interface can include a variety of mechanism but, in general, includes a mechanism for a user to provide input to the processor and for the processor to display status, prompts and results to the user. In a wrist watch embodiment, the user interface may include a series of buttons and an LCD, LED or electroluminescence display. However, it should be appreciated that the present invention is not limited to any particular user interface mechanisms and other technologies can be employed without departing from the spirit and scope of the invention. Such technologies can include voice activations, touch sensitive screens, text to audio conversions and speakers, etc.

The processor 110 includes volatile memory 114 and non-volatile memory 112. The volatile memory 114 may include RAM, EEPROM, bubble memory or other similar technologies and the non-volatile memory may include ROM, EPROM, PROM, Gate Arrays or other similar technologies. The non-volatile memory houses a program including instructions that are executed by the processor. Such instructions provide the intelligence for the processor in responding to inputs from the motion detector 120, the user interface 130 and for controlling the outputs to the user interface 130 and the alarm 140. The volatile memory 114 is used for storing configuration parameters such as the current time, alarm settings, modes of operation or the like.

Figure 2:
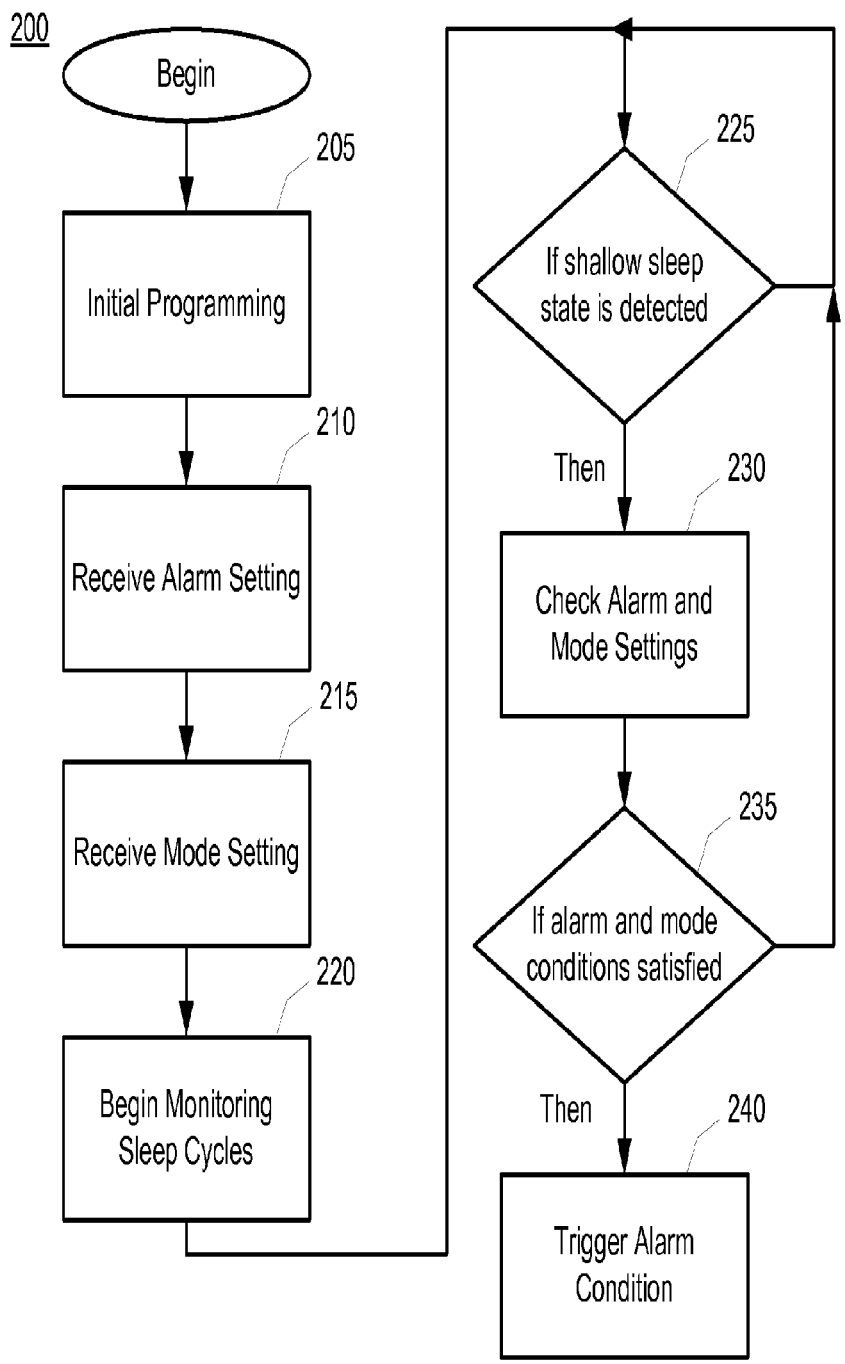
FIG. 2 is a flow diagram illustrating the steps involved in an exemplary embodiment of the present invention.
Figure 3A:
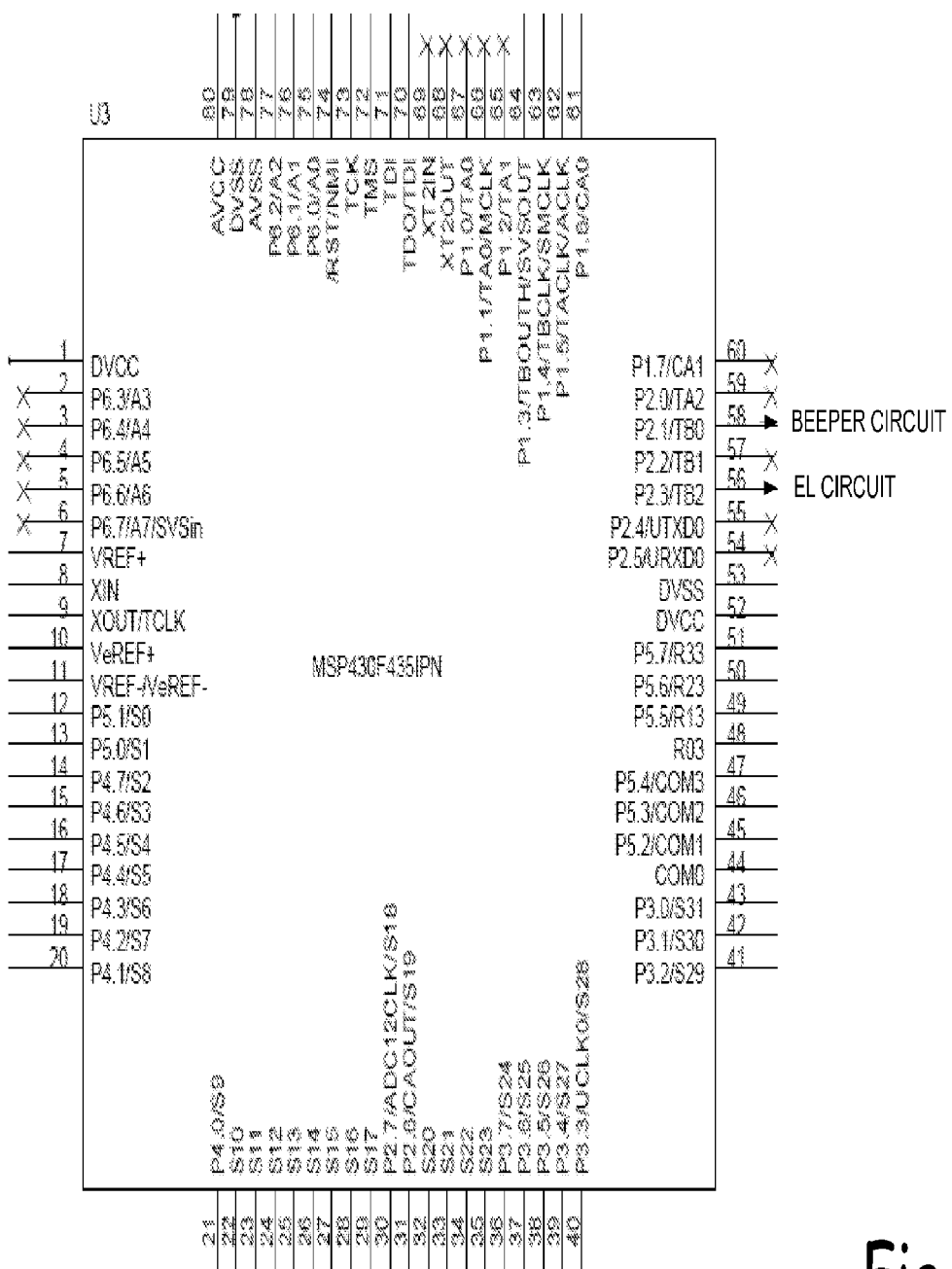
FIG. 3A-3E show a circuit diagram illustrating on technique of implementing the hardware aspect of the present invention.
Figure 3B:
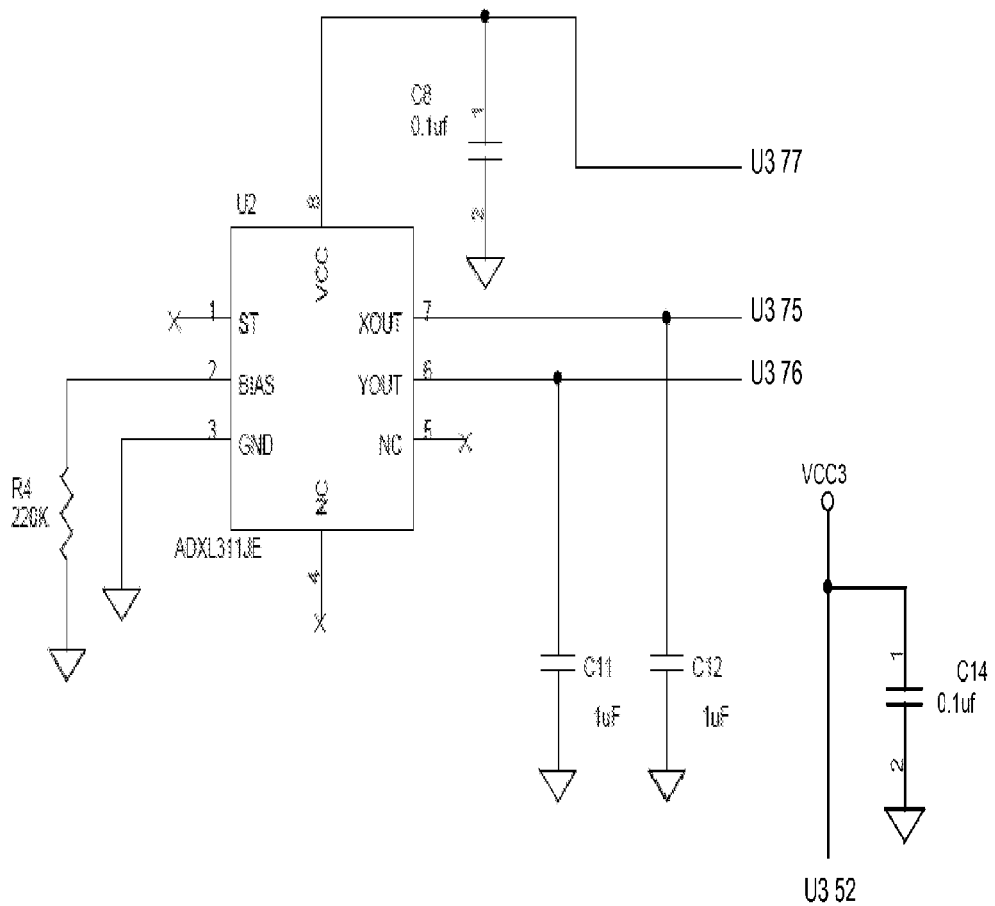
Figure 3C:
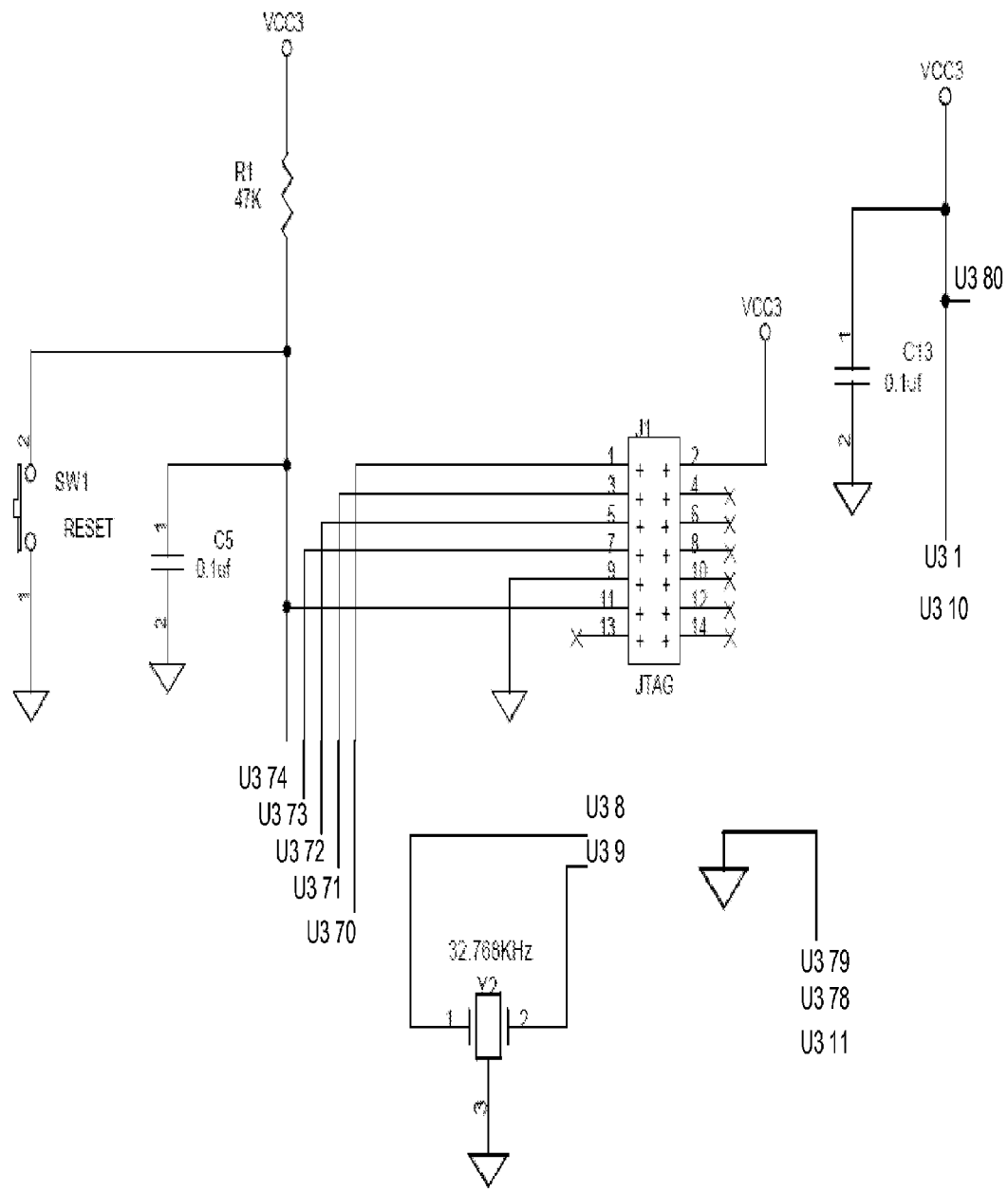
Figure 3D:
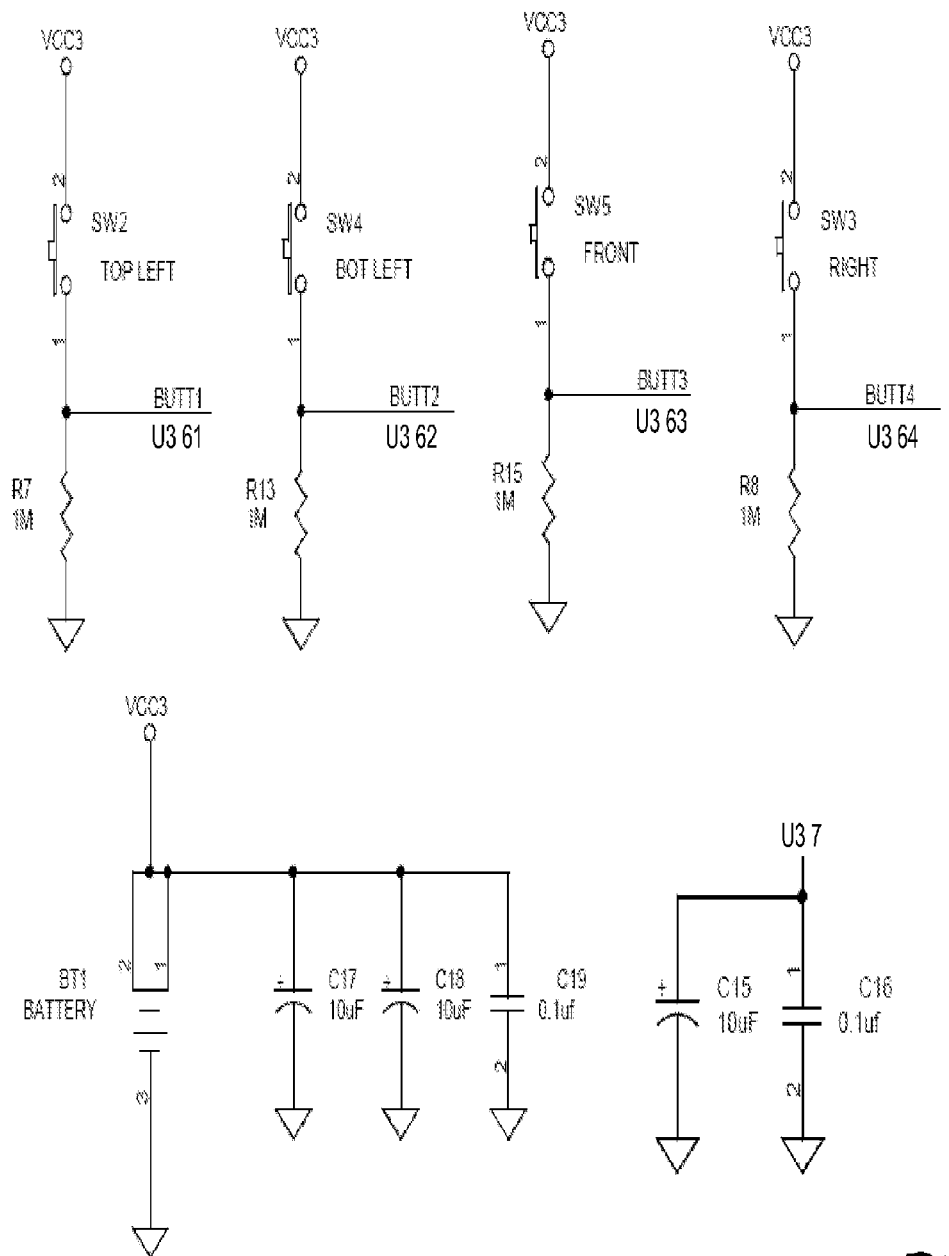
Figure 3E:
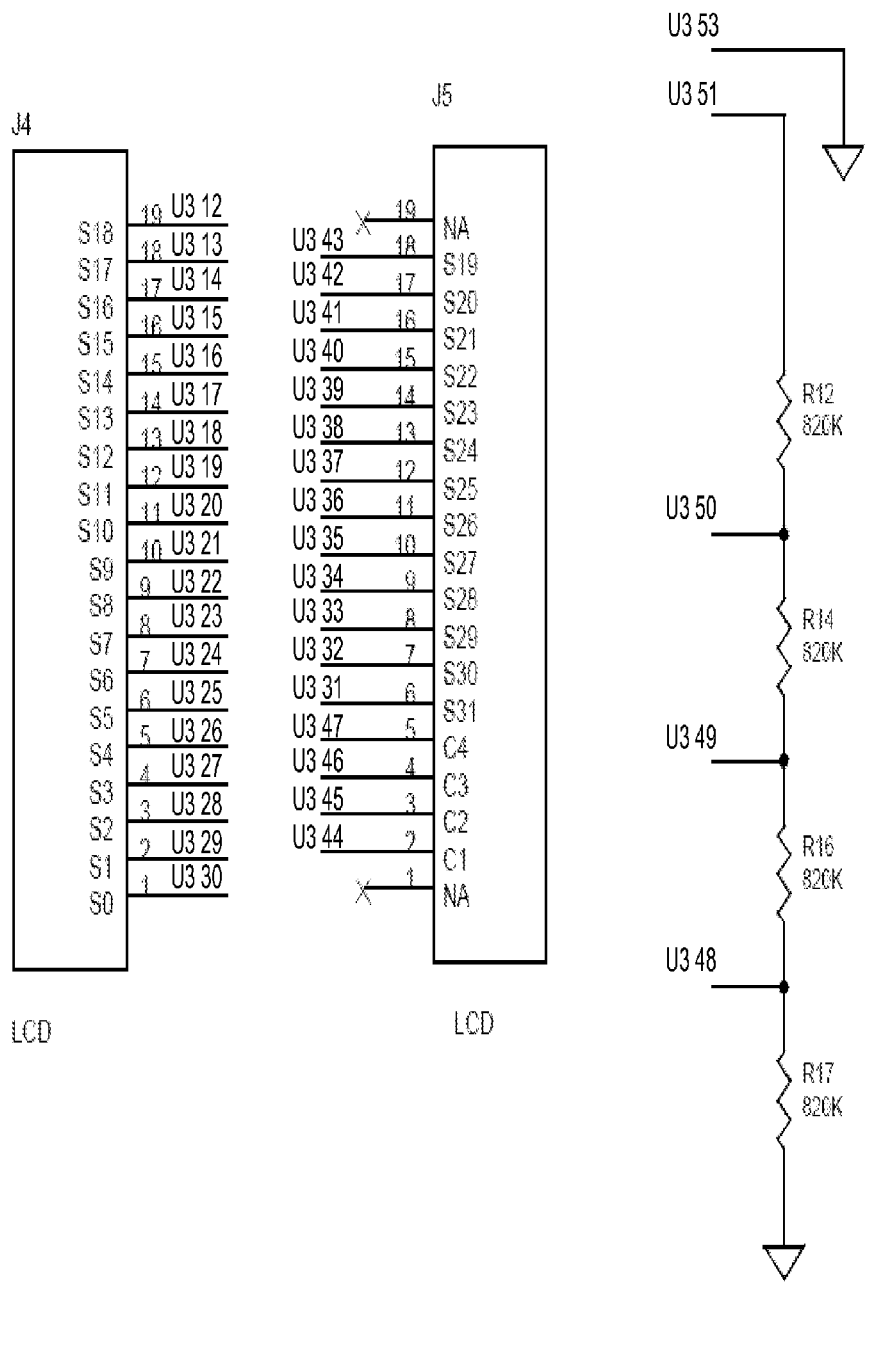

FIG. 2 is a flow diagram illustrating the steps involved in an exemplary embodiment of the present invention. The illustrated process 200 begins by conducting an initial programming 205 of the device 100. The initial programming, among other things, may include a user entering the present local time and date as well as any user configurable parameters such as alarm notifications, text configurations or the like. The user can then program the device 100 with alarm settings 210. As previously described, the alarm settings can include identifying a preferred time to be awakened, a window or threshold period of time, a number of desired sleep cycles or the like. The user can also program the device with mode settings 215. As previously described, the mode settings can include setting the device to wake the user after a predetermined number of sleep cycles, threshold times, or the like. In some embodiments, the alarm settings and the mode settings can be accomplished simultaneously. Once the device 100 is programmed, the device enters into monitoring mode. The monitoring mode 220 can be automatically triggered in accordance with the alarm and mode settings or can be manually triggered by the user when the user retires.

In the monitoring mode, if the processor detects that the user is in a shallow state of sleep 225, such as by receiving an input from the motion detector, the processor checks the alarm and mode settings 230 to determine if the alarm should be sounded. Otherwise, the monitoring mode is continued. If the alarm and mode settings are satisfied 235 (i.e., shallow sleep cycle is detected within the threshold time of the alarm setting or a specified number of sleep cycles is reached), then an alarm is triggered 240. Otherwise, the monitoring mode continues.

FIGS. 3A-3E show a circuit diagram illustrating on technique of implementing the hardware aspect of the present invention. This circuit diagram is provided for informational purposes only and the particular components illustrated and the particular circuitry used in no way limits the present invention. In this example, the MSP430F435IPN device is used to provide the processor and memory elements of the device.

One embodiment of the present invention is used to help children avoid wetting the bed and to help them learn and create habits to avoid such issues. This embodiment of the invention operates similar to the above-described embodiments except that it utilizes three independent alarms rather than just one. One of the issues that give rise to wetting the bed is that a child's bladder may become full during the deep sleep portion of a sleep cycle. In this state, the child is more prone to be in a relaxed state, and as a result, their bodies and or bladders just release the pressure. By getting up a few times in the night, the pressure can be released before it builds up to a full bladder. Advantageously, the child can develop good sleep habits by using this device and even build up the confidence to go dry all night.

Each of the three alarms in this embodiment of the invention includes its own independent window. This embodiment of the invention enables a parent to set the watch to go off up to three times during the night. The device monitors sleep cycles and then attempts to awaken the child when he or she has entered into a light stage of sleep. Thus, in this state, the alarm sounds to awaken the child so that they can get up easily and go to the rest room. The alarm can be audible, as well as a vibration of the child's mattress, turning on of lighting, etc. Advantageously, the child is awakened at a light sleep time and thus, is able to better comprehend what is going on and safely proceed to the bathroom.

As an example, suppose a child is put to bed at 9:00PM. The alarms of the device are programmed as follows:

Alarm 1: 12:00AM;

Alarm 2: 3:00AM; and

Alarm 3: 6:00AM.

Furthermore, the respective windows for each alarm are set to be 60 minutes. Thus, for Alarm 1, anytime between 11:00PM and 12:00AM, if a light stage of sleep is identified, the unit would alarm to wake the child up to use the bathroom.

Window 1: 60 minutes (anytime between 11PM and 12AM if a light stage of sleep was recorded, the unit would go off and the child could get up to use the bathroom)

This embodiment of the present invention allows three or few alarms to be set. Thus, the parent switch from three alarms a night to only two alarms, to one alarm then to no alarms, as they gradually wean the child to sleep though the night. Thus, of the three alarms, the device can be set to where all three alarms or active or, just a subset of the alarms are active.

Another embodiment of the present invention is used to wake up patients to take medicine dosages. Obviously, it could be critical if a patient takes the wrong medicine or the wrong dosage. Thus, the present invention advantageously can operate to awaken the patient at a shallow sleep time, thus awakening them is a more alert and clear thinking state. As a result, the chances of taking wrong medicine or wrong dosages can be reduced in many circumstances.

Figure 5:
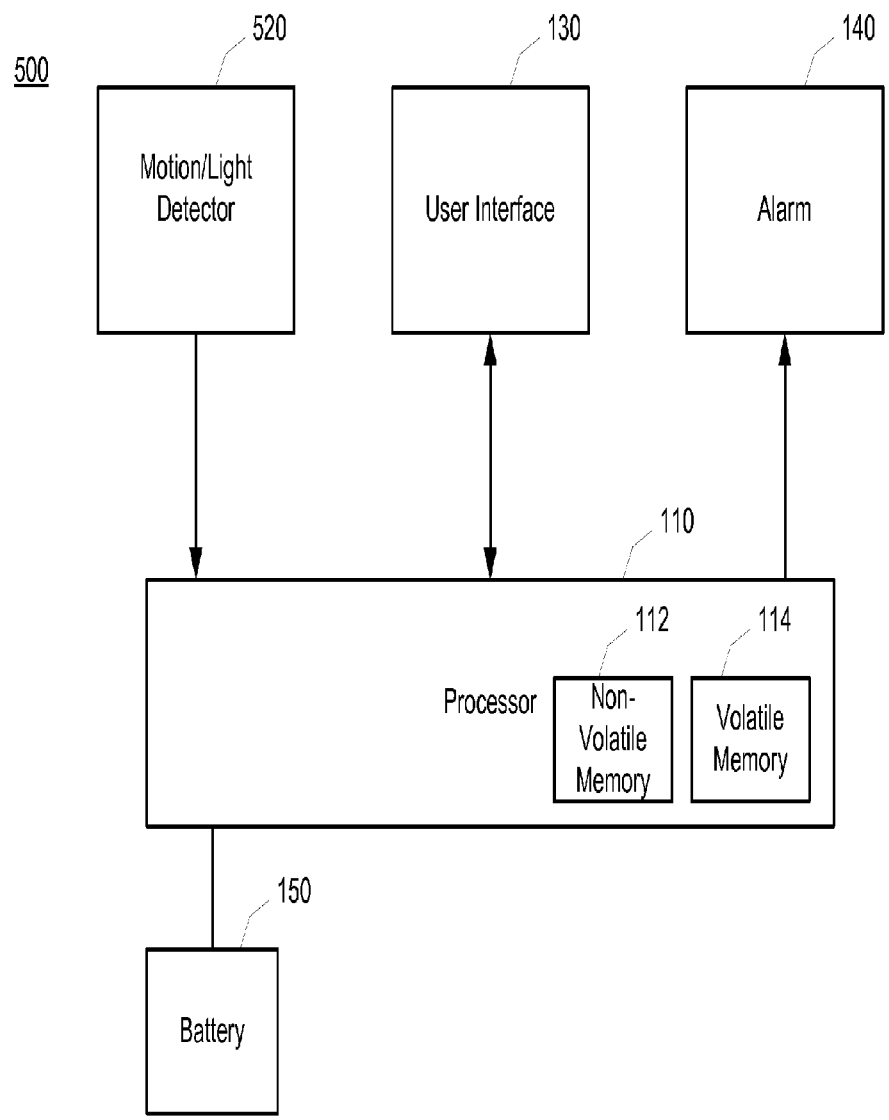
FIG. 5 is a block diagram illustrating the functional components of another exemplary embodiment of the invention.

Another embodiment of the present invention operates in cooperation with the delivery of light therapy for a patient. A light sensor can be incorporated into the various embodiments of the invention to record the amount of light that a patient is exposed to during the day (see element 520 of embodiment 500 in FIG. 5). The device can be programmed to require a certain amount of light exposure during any periodic window, such as everyday or weekly, etc. Thus, the device may include a user programmable variable for a required light amount. In addition, the period of time may default to a particular period, such as a 24 hour period or the user may be able to program a desired period or select from a plurality of preprogrammed period. If the device senses that a user is sleeping but the required amount of light exposure has not been satisfied, UV lamps or other lamps can be illuminated by the device while the patient sleeps. For instance, the patient's room may include a bank of lights that can be controlled by a wireless signal, such as a Bluetooth signal or other RF or infrared signal that is transmitted by the device. Thus, the device can turn on the light source and then turn off the light source, or turn on the light source for a given period of time.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

What is claimed is:

1. An alarm system, the alarm system comprising:
   a single housing that contains an accelerometer, a user interface, a display for rendering the user interface and a processing unit;
   wherein the single housing can be mounted to a body part;
   wherein the accelerometer operates to detect motion on at least one plane;
   wherein the user interface enables a user to program various alarm parameters and settings for the portable alarm system;
   wherein the processing unit is communicatively coupled to the accelerometer and the user interface and, in response to inputs from the accelerometer and the user interface, in cooperation with programming instructions, is operative to:
      receive a user selected alarm setting via the user interface, the alarm setting including an alarm time and a threshold value for at least one alarm;
      monitor the accelerometer for data indicating a positive movement;
      analyze the accelerometer data to establish the timing of sleep cycles and to identify shallow sleep periods of the sleep cycles;
      apply heuristics to estimate the conclusion of a sleep cycle based on sleep cycle data for the user by:
         identifying a typical sleep cycle for the user;
         if a sleep cycle that is substantially longer than the typical sleep cycle for a user is detected, comparing the duration of the long sleep cycle to the typical sleep cycle;
         if the long sleep cycle is approximately a multiple of the typical sleep cycle, concluding that the detection of one or more sleep cycles was missed; and
         incrementing the sleep cycle count in accordance with the estimated number of missed sleep cycles; and
      trigger an alarm condition when a shallow sleep period of a sleep cycle occurs within a threshold of the at least one alarm time.

2. The alarm system of claim 1, wherein the accelerometer detects motion in two planes.

3. An alarm system that can be worn on a user's limb similar to a wrist watch, the portable alarm system comprising:
   a motion detector including an accelerometer;
   a user interface; and
   a processing unit, the processing unit being communicatively coupled to the motion detector and the user interface, and in response to inputs from the motion detector and the user interface, in cooperation with programming instructions, is operative to:
   receive an alarm time setting for up to three alarms with each setting including an alarm time and a threshold value;
   monitor the motion detector for positive movement data indication of the user's limb;
   if the positive movement data indication occurs within a threshold period of time prior to the alarm time, trigger an alarm condition; and
   if no positive movement is detected within a threshold after the alarm time, applying heuristics based on previously received positive movement data to estimate the conclusion of a sleep cycle.

4. A portable alarm system comprising:
   a single housing that contains a user interface, a display for rendering the user interface and a processing unit; and
   an accelerometer operating to detect motion on at least one plane and providing information regarding such detections to the processing unit;
   wherein the user interface enables a user to program various alarm parameters and settings for the portable alarm system; and
   wherein the processing unit is communicatively coupled to the accelerometer and the user interface and, in response to inputs from the accelerometer and the user interface, in cooperation with programming instructions, is operative to:
      receive user selected alarm settings via the user interface, the alarm setting including a sleep cycle count value for at least one alarm;
      monitor the accelerometer for data indicating a positive movement;
      analyze the accelerometer data to establish the timing of sleep cycles and to identify shallow sleep periods of the sleep cycles;
      identify a typical sleep cycle for the user;
      increment a sleep cycle counter for each detected sleep cycle;
      if a sleep cycle is detected that is substantially longer than the typical sleep cycle for a user, compare the duration of the long sleep cycle to the typical sleep cycle;
      if the long sleep cycle is approximately a multiple of the typical sleep cycle, conclude that the detection of one or more sleep cycles was missed;
      increment a sleep cycle counter in accordance with the estimated number of missed sleep cycles; and
      when the sleep cycle counter reaches a sleep cycle count value, trigger an alarm.

5. The portable alarm system of claim 4, wherein the accelerometer is incorporated into the single housing.

6. The portable alarm system of claim 4, wherein the accelerometer is incorporated into a mattress.

7. The portable alarm system of claim 6, further comprising pressure detection devices.

8. The portable alarm system of claim 4, further comprising a radio frequency technology interface to transmit an alarm signal to turn on a remote device to sound an alarm.

9. The portable alarm system of claim 4, further comprising a light sensor operable to record the amount of light the device has been exposed to during a selected period, and a transmitter, and further comprising a programmed required light amount, wherein if the device detects that that user is in a sleeping state but the programmed required light amount has not been reached, transmitting a signal using the transmitter, the signal being operative to turn on an external light source.

10. The portable alarm system of claim 9, wherein the device is further operative to transmit a signal to turn off the external light source.

11. A portable apparatus in a single housing that can be worn on a user's limb, the portable apparatus comprising:
   an accelerometer for detecting motion in at least one plane;
   a user interface including a display for rendering the user interface and an input interface enabling a user to program at least one alarm setting with each setting including alarm triggering parameters; and
   a processing unit communicatively coupled to the accelerometer and the user interface, and being operative to:
      monitor the accelerometer for signals indicating a positive movement;
      analyze the accelerometer data to establish the timing of sleep cycles and to identify shallow sleep periods of the sleep cycles;

apply heuristics to estimate the conclusion of a sleep cycle based on sleep cycle data for the user by:
  identifying a typical sleep cycle for the user;
    if a sleep cycle that is substantially longer than the typical sleep cycle for a user is detected, comparing the duration of the long sleep cycle to the typical sleep cycle; and
    if the long sleep cycle is approximately a multiple of the typical sleep cycle, concluding that the detection of one or more sleep cycles was missed; and
  trigger an alarm condition in accordance with the alarm triggering parameters proximate to a shallow sleep period of a sleep cycle.

12. The portable apparatus of claim 11, wherein the alarm triggering parameters include an alarm time and an associated threshold, and triggering an alarm condition in accordance with the alarm triggering parameters includes triggering an alarm condition when a shallow sleep cycle is within the threshold of the alarm time.

13. The portable apparatus of claim 11, wherein the alarm triggering parameters include a sleep cycle count, and concluding that the detection of one or more sleep cycles was missed includes incrementing a sleep cycle count accordingly and triggering an alarm condition in accordance with the alarm triggering parameters includes triggering an alarm condition at a shallow sleep cycle that occurs commensurate with the sleep cycle count.

14. The portable apparatus of claim 11, further comprising a light sensor operable to record the amount of light the device has been exposed to during a selected period, and a transmitter, and further comprising a programmed required light amount, wherein if the device detects that that user is in a sleeping state but the programmed required light amount has not been reached, transmitting a signal using the transmitter, the signal being operative to turn on an external light source.

15. A portable apparatus used in proximity to a user, the portable apparatus comprising:
  an accelerometer for detecting motion in at least one plane;
  a user interface including a display for rendering the user interface and an input interface enabling a user to program at least one alarm setting, wherein each alarm setting includes alarm triggering parameters; and
  at least one processing unit communicatively coupled to the accelerometer and the user interface, wherein the at least one processing unit is operative to:
    monitor the accelerometer for signals indicating a positive movement;
    analyze the accelerometer data to establish the timing of sleep cycles and to identify shallow sleep periods of the sleep cycles; and
    trigger an alarm condition in accordance with the alarm triggering parameters proximate to a shallow sleep period of a sleep cycle and the application of heuristics to estimate the conclusion of a sleep cycle based on sleep cycle data for the user by:
      identifying a typical sleep cycle for the user;
      determining that the sleep cycle is longer than the typical sleep cycle for the user by comparing the duration of the sleep cycle to the typical sleep cycle, wherein if the sleep cycle is approximately a multiple of the typical sleep cycle, concluding that the detection of one or more sleep cycles was missed.

16. The portable apparatus of claim 15, wherein:
  the alarm triggering parameters include a sleep cycle count;
  concluding that the detection of one or more sleep cycles was missed includes incrementing a sleep cycle count accordingly; and
  triggering an alarm condition in accordance with the alarm triggering parameters includes triggering an alarm condition at a shallow sleep cycle that occurs commensurate with the sleep cycle count.

17. An alarm system that can detect sleep cycles of an individual, the alarm system comprising:
  a motion detector including an accelerometer;
  a user interface; and
  a processing unit, the processing unit being communicatively coupled to the motion detector and the user interface, and in response to inputs from the motion detector and the user interface, in cooperation with programming instructions, is configured to:
    receive an alarm time setting for up to three alarms with each setting including an alarm time and a threshold value;
    monitor the motion detector for positive movement data indication of the user's limb;
    if the positive movement data indication occurs within a threshold period of time prior to the alarm time, trigger an alarm condition; and
    if no positive movement is detected within a threshold after the alarm time, applying heuristics based on previously received positive movement data to estimate the conclusion of a sleep cycle.

* * * * *